United States Patent
Wong et al.

(10) Patent No.: US 10,214,738 B2
(45) Date of Patent: *Feb. 26, 2019

(54) PRODUCTION OF HIGH PURITY CHONDROITINASE ABC

(71) Applicant: Advantek Serum Laboratories Ltd., Hong Kong (HK)

(72) Inventors: Bing Lou Wong, Irvine, CA (US); Wai Hong Chung, Hong Kong (HK)

(73) Assignee: Advantek Serum Laboratories Ltd., Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 16/048,362

(22) Filed: Jul. 30, 2018

(65) Prior Publication Data

US 2018/0327735 A1    Nov. 15, 2018

Related U.S. Application Data

(62) Division of application No. 15/788,824, filed on Oct. 20, 2017, now Pat. No. 10,036,004, which is a division of application No. 15/494,589, filed on Apr. 24, 2017, now Pat. No. 9,796,970.

(51) Int. Cl.
  *C12N 9/88* (2006.01)
  *B01D 15/38* (2006.01)

(52) U.S. Cl.
  CPC ........... *C12N 9/88* (2013.01); *B01D 15/3804* (2013.01); *C12Y 402/02004* (2013.01)

(58) Field of Classification Search
  None
  See application file for complete search history.

(56) References Cited

PUBLICATIONS

UniProtKB/Swiss-Prot Accession No. P59807 (available since Aug. 15, 2003, retrieved from the internet: <<https://www.uniprot.org/uniprot/P59807.txt>>, retrieved on Sep. 26, 2018).*
Liao et al. (Removal of N-terminal methionine from recombinant proteins by engineered *E. coli* methionine aminopeptidase, Protein Science (2004), 13:1802-1810).*
International Search Report of PCT/US2018/028214 dated Aug. 8, 2018.
International Search Report and Written Opinion dated Aug. 8, 2018 for a corresponding PCT application under the application No. PCT/US2018/028214 filed Apr. 19, 2018.

* cited by examiner

*Primary Examiner* — Suzanne M Noakes
*Assistant Examiner* — Jae W Lee
(74) *Attorney, Agent, or Firm* — Idea Intellectual Limited; Margaret A. Burke; Sam T. Yip

(57) ABSTRACT

The present invention provides a method for purifying Chondroitinase ABC (ChABC). The present method includes using a heparin-immobilized affinity chromatography column, and through chromatography method obtaining a purified ChABC from a matrix containing the ChABC. The present method is capable of obtaining ChABC in high purity with the advantages of simplicity in preparation and high yield.

9 Claims, 7 Drawing Sheets

Specification includes a Sequence Listing.

SEQUENCE LISTING

<160> NUMBER OF SEQ ID NOS: 3

<210> SEQ ID NO 1
<211> LENGTH: 997
<212> TYPE: PRT
<213> ORGANISM: Proteus vulgaris

<400> SEQUENCE: 1

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Pro Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Ala Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Ile His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365
```

-continued

```
Ser Ser Arg Trp Trp Tyr Ile Ser Thr Leu Leu Met Ser Asp Ala Leu
370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
            405                 410                 415

Ser Asp Leu Asp Tyr Phe Asn Thr Leu Ser Arg Gln His Leu Ala Leu
            420                 425                 430

Leu Leu Leu Glu Pro Asp Gln Lys Arg Ile Asn Leu Val Asn Thr
        435                 440                 445

Phe Ser His Tyr Ile Thr Gly Ala Leu Thr Gln Val Pro Pro Gly Gly
450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
            485                 490                 495

Tyr Leu Leu Arg Asp Thr Pro Phe Ser Val Gly Glu Ser Gly Trp Asn
            500                 505                 510

Asn Leu Lys Lys Ala Met Val Ser Ala Trp Ile Tyr Ser Asn Pro Glu
        515                 520                 525

Val Gly Leu Pro Leu Ala Gly Arg His Pro Phe Asn Ser Pro Ser Leu
530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
            565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
            645                 650                 655

Gln Gly Tyr Gln Gln Glu Gly Trp Asp Trp Asn Arg Met Gln Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
            725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
770                 775                 780

Tyr Gln Thr Thr Leu Gln Gln Gly Asp Trp Leu Ile Asp Ser Asn Gly
```

```
                        785                 790                 795                 800
Asn Gly Tyr Leu Ile Thr Gln Ala Glu Lys Val Asn Val Ser Arg Gln
                    805                 810                 815

His Gln Val Ser Ala Glu Asn Lys Asn Arg Gln Pro Thr Glu Gly Asn
                820                 825                 830

Phe Ser Ser Ala Trp Ile Asp His Ser Thr Arg Pro Lys Asp Ala Ser
            835                 840                 845

Tyr Glu Tyr Met Val Phe Leu Asp Ala Thr Pro Glu Lys Met Gly Glu
        850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro
        995

<210> SEQ ID NO 2
<211> LENGTH: 998
<212> TYPE: PRT
<213> ORGANISM: Artificial Sequence
<220> FEATURE:
<223> OTHER INFORMATION: The sequence is synthesized

<400> SEQUENCE: 2

Met Ala Thr Ser Asn Pro Ala Phe Asp Pro Lys Asn Leu Met Gln Ser
1               5                   10                  15

Glu Ile Tyr His Phe Ala Gln Asn Asn Pro Leu Ala Asp Phe Ser Ser
                20                  25                  30

Asp Lys Asn Ser Ile Leu Thr Leu Ser Asp Lys Arg Ser Ile Met Gly
            35                  40                  45

Asn Gln Ser Leu Leu Trp Lys Trp Lys Gly Gly Ser Ser Phe Thr Leu
        50                  55                  60

His Lys Lys Leu Ile Val Pro Thr Asp Lys Glu Ala Ser Lys Ala Trp
65                  70                  75                  80

Gly Arg Ser Ser Thr Pro Val Phe Ser Phe Trp Leu Tyr Asn Glu Lys
                85                  90                  95

Pro Ile Asp Gly Tyr Pro Thr Ile Asp Phe Gly Glu Lys Leu Ile Ser
            100                 105                 110

Thr Ser Glu Ala Gln Ala Gly Phe Lys Val Lys Leu Asp Phe Thr Gly
        115                 120                 125

Trp Arg Ala Val Gly Val Ser Leu Asn Asp Leu Glu Asn Arg Glu
    130                 135                 140

Met Thr Leu Asn Ala Thr Asn Thr Ser Ser Asp Gly Thr Gln Asp Ser
```

-continued

```
            145                 150                 155                 160
Ile Gly Arg Ser Leu Gly Ala Lys Val Asp Ser Ile Arg Phe Lys Ala
                165                 170                 175

Pro Ser Asn Val Ser Gln Gly Glu Ile Tyr Ile Asp Arg Ile Met Phe
                180                 185                 190

Ser Val Asp Asp Ala Arg Tyr Gln Trp Ser Asp Tyr Gln Val Lys Thr
                195                 200                 205

Arg Leu Ser Glu Pro Glu Ile Gln Phe His Asn Val Lys Pro Gln Leu
            210                 215                 220

Pro Val Thr Pro Glu Asn Leu Ala Ala Ile Asp Leu Ile Arg Gln Arg
225                 230                 235                 240

Leu Ile Asn Glu Phe Val Gly Gly Glu Lys Glu Thr Asn Leu Ala Leu
                245                 250                 255

Glu Glu Asn Ile Ser Lys Leu Lys Ser Asp Phe Asp Ala Leu Asn Ile
                260                 265                 270

His Thr Leu Ala Asn Gly Gly Thr Gln Gly Arg His Leu Ile Thr Asp
            275                 280                 285

Lys Gln Ile Ile Tyr Gln Pro Glu Asn Leu Asn Ser Gln Asp Lys
            290                 295                 300

Gln Leu Phe Asp Asn Tyr Val Ile Leu Gly Asn Tyr Thr Thr Leu Met
305                 310                 315                 320

Phe Asn Ile Ser Arg Ala Tyr Val Leu Glu Lys Asp Pro Thr Gln Lys
                325                 330                 335

Ala Gln Leu Lys Gln Met Tyr Leu Leu Met Thr Lys His Leu Leu Asp
                340                 345                 350

Gln Gly Phe Val Lys Gly Ser Ala Leu Val Thr Thr His His Trp Gly
            355                 360                 365

Tyr Ser Ser Arg Trp Trp Tyr Ile Ser Thr Leu Leu Met Ser Asp Ala
            370                 375                 380

Leu Lys Glu Ala Asn Leu Gln Thr Gln Val Tyr Asp Ser Leu Leu Trp
385                 390                 395                 400

Tyr Ser Arg Glu Phe Lys Ser Ser Phe Asp Met Lys Val Ser Ala Asp
                405                 410                 415

Ser Ser Asp Leu Asp Tyr Phe Asn Thr Leu Ser Arg Gln His Leu Ala
                420                 425                 430

Leu Leu Leu Leu Glu Pro Asp Asp Gln Lys Arg Ile Asn Leu Val Asn
            435                 440                 445

Thr Phe Ser His Tyr Ile Thr Gly Ala Leu Thr Gln Val Pro Pro Gly
            450                 455                 460

Gly Lys Asp Gly Leu Arg Pro Asp Gly Thr Ala Trp Arg His Glu Gly
465                 470                 475                 480

Asn Tyr Pro Gly Tyr Ser Phe Pro Ala Phe Lys Asn Ala Ser Gln Leu
                485                 490                 495

Ile Tyr Leu Leu Arg Asp Thr Pro Phe Ser Val Gly Glu Ser Gly Trp
            500                 505                 510

Asn Asn Leu Lys Lys Ala Met Val Ser Ala Trp Ile Tyr Ser Asn Pro
            515                 520                 525

Glu Val Gly Leu Pro Leu Ala Gly Arg His Pro Phe Asn Ser Pro Ser
            530                 535                 540

Leu Lys Ser Val Ala Gln Gly Tyr Tyr Trp Leu Ala Met Ser Ala Lys
545                 550                 555                 560

Ser Ser Pro Asp Lys Thr Leu Ala Ser Ile Tyr Leu Ala Ile Ser Asp
                565                 570                 575
```

```
Lys Thr Gln Asn Glu Ser Thr Ala Ile Phe Gly Glu Thr Ile Thr Pro
            580                 585                 590

Ala Ser Leu Pro Gln Gly Phe Tyr Ala Phe Asn Gly Ala Phe Gly
        595                 600                 605

Ile His Arg Trp Gln Asp Lys Met Val Thr Leu Lys Ala Tyr Asn Thr
610                 615                 620

Asn Val Trp Ser Ser Glu Ile Tyr Asn Lys Asp Asn Arg Tyr Gly Arg
625                 630                 635                 640

Tyr Gln Ser His Gly Val Ala Gln Ile Val Ser Asn Gly Ser Gln Leu
                645                 650                 655

Ser Gln Gly Tyr Gln Gln Glu Gly Trp Asp Trp Asn Arg Met Gln Gly
            660                 665                 670

Ala Thr Thr Ile His Leu Pro Leu Lys Asp Leu Asp Ser Pro Lys Pro
        675                 680                 685

His Thr Leu Met Gln Arg Gly Glu Arg Gly Phe Ser Gly Thr Ser Ser
    690                 695                 700

Leu Glu Gly Gln Tyr Gly Met Met Ala Phe Asp Leu Ile Tyr Pro Ala
705                 710                 715                 720

Asn Leu Glu Arg Phe Asp Pro Asn Phe Thr Ala Lys Lys Ser Val Leu
                725                 730                 735

Ala Ala Asp Asn His Leu Ile Phe Ile Gly Ser Asn Ile Asn Ser Ser
            740                 745                 750

Asp Lys Asn Lys Asn Val Glu Thr Thr Leu Phe Gln His Ala Ile Thr
        755                 760                 765

Pro Thr Leu Asn Thr Leu Trp Ile Asn Gly Gln Lys Ile Glu Asn Met
    770                 775                 780

Pro Tyr Gln Thr Thr Leu Gln Gln Gly Asp Trp Leu Ile Asp Ser Asn
785                 790                 795                 800

Gly Asn Gly Tyr Leu Ile Thr Gln Ala Glu Lys Val Asn Val Ser Arg
                805                 810                 815

Gln His Gln Val Ser Ala Glu Asn Lys Asn Arg Gln Pro Thr Glu Gly
            820                 825                 830

Asn Phe Ser Ser Ala Trp Ile Asp His Ser Thr Arg Pro Lys Asp Ala
        835                 840                 845

Ser Tyr Glu Tyr Met Val Phe Leu Asp Ala Thr Pro Glu Lys Met Gly
    850                 855                 860

Glu Met Ala Gln Lys Phe Arg Glu Asn Asn Gly Leu Tyr Gln Val Leu
865                 870                 875                 880

Arg Lys Asp Lys Asp Val His Ile Ile Leu Asp Lys Leu Ser Asn Val
                885                 890                 895

Thr Gly Tyr Ala Phe Tyr Gln Pro Ala Ser Ile Glu Lys Trp Ile
            900                 905                 910

Lys Lys Val Asn Lys Pro Ala Ile Val Met Thr His Arg Gln Lys Asp
        915                 920                 925

Thr Leu Ile Val Ser Ala Val Thr Pro Asp Leu Asn Met Thr Arg Gln
    930                 935                 940

Lys Ala Ala Thr Pro Val Thr Ile Asn Val Thr Ile Asn Gly Lys Trp
945                 950                 955                 960

Gln Ser Ala Asp Lys Asn Ser Glu Val Lys Tyr Gln Val Ser Gly Asp
                965                 970                 975

Asn Thr Glu Leu Thr Phe Thr Ser Tyr Phe Gly Ile Pro Gln Glu Ile
            980                 985                 990
```

Lys Leu Ser Pro Leu Pro
              995

<210> SEQ ID NO 3
<211> LENGTH: 1006
<212> TYPE: PRT
<213> ORGANISM: Artificial Sequence
<220> FEATURE:
<223> OTHER INFORMATION: The sequence is synthesized

<400> SEQUENCE: 3

Met Gly Ser Glu Asn Leu Tyr Phe Gln Ala Thr Ser Asn Pro Ala Phe
1               5                   10                  15

Asp Pro Lys Asn Leu Met Gln Ser Glu Ile Tyr His Phe Ala Gln Asn
            20                  25                  30

Asn Pro Leu Ala Asp Phe Ser Ser Asp Lys Asn Ser Ile Leu Thr Leu
        35                  40                  45

Ser Asp Lys Arg Ser Ile Met Gly Asn Gln Ser Leu Leu Trp Lys Trp
50                  55                  60

Lys Gly Gly Ser Ser Phe Thr Leu His Lys Lys Leu Ile Val Pro Thr
65                  70                  75                  80

Asp Lys Glu Ala Ser Lys Ala Trp Gly Arg Ser Ser Thr Pro Val Phe
            85                  90                  95

Ser Phe Trp Leu Tyr Asn Glu Lys Pro Ile Asp Gly Tyr Pro Thr Ile
        100                 105                 110

Asp Phe Gly Glu Lys Leu Ile Ser Thr Ser Glu Ala Gln Ala Gly Phe
    115                 120                 125

Lys Val Lys Leu Asp Phe Thr Gly Trp Arg Ala Val Gly Val Ser Leu
130                 135                 140

Asn Asn Asp Leu Glu Asn Arg Glu Met Thr Leu Asn Ala Thr Asn Thr
145                 150                 155                 160

Ser Ser Asp Gly Thr Gln Asp Ser Ile Gly Arg Ser Leu Gly Ala Lys
                165                 170                 175

Val Asp Ser Ile Arg Phe Lys Ala Pro Ser Asn Val Ser Gln Gly Glu
            180                 185                 190

Ile Tyr Ile Asp Arg Ile Met Phe Ser Val Asp Ala Arg Tyr Gln
        195                 200                 205

Trp Ser Asp Tyr Gln Val Lys Thr Arg Leu Ser Glu Pro Glu Ile Gln
210                 215                 220

Phe His Asn Val Lys Pro Gln Leu Pro Val Thr Pro Glu Asn Leu Ala
225                 230                 235                 240

Ala Ile Asp Leu Ile Arg Gln Arg Leu Ile Asn Glu Phe Val Gly Gly
                245                 250                 255

Glu Lys Glu Thr Asn Leu Ala Leu Glu Glu Asn Ile Ser Lys Leu Lys
            260                 265                 270

Ser Asp Phe Asp Ala Leu Asn Ile His Thr Leu Ala Asn Gly Gly Thr
        275                 280                 285

Gln Gly Arg His Leu Ile Thr Asp Lys Gln Ile Ile Tyr Gln Pro
    290                 295                 300

Glu Asn Leu Asn Ser Gln Asp Lys Gln Leu Phe Asp Asn Tyr Val Ile
305                 310                 315                 320

Leu Gly Asn Tyr Thr Thr Leu Met Phe Asn Ile Ser Arg Ala Tyr Val
                325                 330                 335

Leu Glu Lys Asp Pro Thr Gln Lys Ala Gln Leu Lys Gln Met Tyr Leu
            340                 345                 350

-continued

Leu Met Thr Lys His Leu Asp Gln Gly Phe Val Lys Gly Ser Ala
    355                 360                 365

Leu Val Thr Thr His His Trp Gly Tyr Ser Ser Arg Trp Trp Tyr Ile
370                 375                 380

Ser Thr Leu Leu Met Ser Asp Ala Leu Lys Glu Ala Asn Leu Gln Thr
385                 390                 395                 400

Gln Val Tyr Asp Ser Leu Leu Trp Tyr Ser Arg Glu Phe Lys Ser Ser
                405                 410                 415

Phe Asp Met Lys Val Ser Ala Asp Ser Ser Asp Leu Asp Tyr Phe Asn
            420                 425                 430

Thr Leu Ser Arg Gln His Leu Ala Leu Leu Leu Glu Pro Asp Asp
        435                 440                 445

Gln Lys Arg Ile Asn Leu Val Asn Thr Phe Ser His Tyr Ile Thr Gly
    450                 455                 460

Ala Leu Thr Gln Val Pro Pro Gly Gly Lys Asp Gly Leu Arg Pro Asp
465                 470                 475                 480

Gly Thr Ala Trp Arg His Glu Gly Asn Tyr Pro Gly Tyr Ser Phe Pro
                485                 490                 495

Ala Phe Lys Asn Ala Ser Gln Leu Ile Tyr Leu Leu Arg Asp Thr Pro
            500                 505                 510

Phe Ser Val Gly Glu Ser Gly Trp Asn Asn Leu Lys Lys Ala Met Val
        515                 520                 525

Ser Ala Trp Ile Tyr Ser Asn Pro Glu Val Gly Leu Pro Leu Ala Gly
    530                 535                 540

Arg His Pro Phe Asn Ser Pro Ser Leu Lys Ser Val Ala Gln Gly Tyr
545                 550                 555                 560

Tyr Trp Leu Ala Met Ser Ala Lys Ser Ser Pro Asp Lys Thr Leu Ala
                565                 570                 575

Ser Ile Tyr Leu Ala Ile Ser Asp Lys Thr Gln Asn Glu Ser Thr Ala
            580                 585                 590

Ile Phe Gly Glu Thr Ile Thr Pro Ala Ser Leu Pro Gln Gly Phe Tyr
        595                 600                 605

Ala Phe Asn Gly Gly Ala Phe Gly Ile His Arg Trp Gln Asp Lys Met
    610                 615                 620

Val Thr Leu Lys Ala Tyr Asn Thr Asn Val Trp Ser Ser Glu Ile Tyr
625                 630                 635                 640

Asn Lys Asp Asn Arg Tyr Gly Arg Tyr Gln Ser His Gly Val Ala Gln
                645                 650                 655

Ile Val Ser Asn Gly Ser Gln Leu Ser Gln Gly Tyr Gln Gln Glu Gly
            660                 665                 670

Trp Asp Trp Asn Arg Met Gln Gly Ala Thr Thr Ile His Leu Pro Leu
        675                 680                 685

Lys Asp Leu Asp Ser Pro Lys Pro His Thr Leu Met Gln Arg Gly Glu
    690                 695                 700

Arg Gly Phe Ser Gly Thr Ser Leu Glu Gly Gln Tyr Gly Met Met
705                 710                 715                 720

Ala Phe Asp Leu Ile Tyr Pro Ala Asn Leu Glu Arg Phe Asp Pro Asn
                725                 730                 735

Phe Thr Ala Lys Lys Ser Val Leu Ala Ala Asp Asn His Leu Ile Phe
            740                 745                 750

Ile Gly Ser Asn Ile Asn Ser Ser Asp Lys Asn Lys Asn Val Glu Thr
        755                 760                 765

Thr Leu Phe Gln His Ala Ile Thr Pro Thr Leu Asn Thr Leu Trp Ile

|   |   |   | 770 |   |   |   | 775 |   |   |   | 780 |   |
|---|---|---|---|---|---|---|---|---|---|---|---|---|
| Asn | Gly | Gln | Lys | Ile | Glu | Asn | Met | Pro | Tyr | Gln | Thr | Thr | Leu | Gln | Gln |
| 785 |   |   |   |   | 790 |   |   |   |   | 795 |   |   |   |   | 800 |
| Gly | Asp | Trp | Leu | Ile | Asp | Ser | Asn | Gly | Asn | Gly | Tyr | Leu | Ile | Thr | Gln |
|   |   |   |   | 805 |   |   |   |   | 810 |   |   |   |   | 815 |   |
| Ala | Glu | Lys | Val | Asn | Val | Ser | Arg | Gln | His | Gln | Val | Ser | Ala | Glu | Asn |
|   |   |   | 820 |   |   |   |   | 825 |   |   |   |   | 830 |   |   |
| Lys | Asn | Arg | Gln | Pro | Thr | Glu | Gly | Asn | Phe | Ser | Ser | Ala | Trp | Ile | Asp |
|   |   | 835 |   |   |   |   | 840 |   |   |   |   | 845 |   |   |   |
| His | Ser | Thr | Arg | Pro | Lys | Asp | Ala | Ser | Tyr | Glu | Tyr | Met | Val | Phe | Leu |
|   | 850 |   |   |   | 855 |   |   |   |   | 860 |   |   |   |   |   |
| Asp | Ala | Thr | Pro | Glu | Lys | Met | Gly | Glu | Met | Ala | Gln | Lys | Phe | Arg | Glu |
| 865 |   |   |   | 870 |   |   |   |   | 875 |   |   |   |   |   | 880 |
| Asn | Asn | Gly | Leu | Tyr | Gln | Val | Leu | Arg | Lys | Asp | Lys | Asp | Val | His | Ile |
|   |   |   |   | 885 |   |   |   |   | 890 |   |   |   |   | 895 |   |
| Ile | Leu | Asp | Lys | Leu | Ser | Asn | Val | Thr | Gly | Tyr | Ala | Phe | Tyr | Gln | Pro |
|   |   |   | 900 |   |   |   |   | 905 |   |   |   |   | 910 |   |   |
| Ala | Ser | Ile | Glu | Asp | Lys | Trp | Ile | Lys | Lys | Val | Asn | Lys | Pro | Ala | Ile |
|   |   | 915 |   |   |   |   | 920 |   |   |   |   | 925 |   |   |   |
| Val | Met | Thr | His | Arg | Gln | Lys | Asp | Thr | Leu | Ile | Val | Ser | Ala | Val | Thr |
|   | 930 |   |   |   |   | 935 |   |   |   |   | 940 |   |   |   |   |
| Pro | Asp | Leu | Asn | Met | Thr | Arg | Gln | Lys | Ala | Ala | Thr | Pro | Val | Thr | Ile |
| 945 |   |   |   |   | 950 |   |   |   |   | 955 |   |   |   |   | 960 |
| Asn | Val | Thr | Ile | Asn | Gly | Lys | Trp | Gln | Ser | Ala | Asp | Lys | Asn | Ser | Glu |
|   |   |   |   | 965 |   |   |   |   | 970 |   |   |   |   | 975 |   |
| Val | Lys | Tyr | Gln | Val | Ser | Gly | Asp | Asn | Thr | Glu | Leu | Thr | Phe | Thr | Ser |
|   |   |   | 980 |   |   |   |   | 985 |   |   |   |   | 990 |   |   |
| Tyr | Phe | Gly | Ile | Pro | Gln | Glu | Ile |  | Lys | Leu | Ser | Pro | Leu |  | Pro |
|   |   | 995 |   |   |   |   | 1000 |   |   |   |   |   | 1005 |   |   |

PRODUCTION OF HIGH PURITY CHONDROITINASE ABC

CROSS-REFERENCE TO RELATED APPLICATIONS

This application is a divisional application of U.S. nonprovisional patent application Ser. No. 15/788,824 filed Oct. 20, 2017, which is a divisional application of U.S. nonprovisional patent application Ser. No. 15/494,589 filed Apr. 24, 2017 (now patented under the U.S. Pat. No. 9,796,970), and the disclosures of which are incorporated herein by reference in their entirety.

FIELD OF THE INVENTION

The present invention relates to a process for the purification of chondroitinase ABC (ChABC), and more particularly to a method for purifying ChABC from a matrix containing ChABC by affinity chromatography.

BACKGROUND

Chondroitinase ABC (ChABC) is an enzyme that catalyzes chemical reactions involving the eliminative degradation of polysaccharides containing 1,4-beta-D-hexosaminyl and 1,3-beta-D-glucuronosyl or 1,3-alpha-L-iduronosyl linkages to disaccharides containing 4-deoxy-beta-D-gluc-4-enuronosyl groups. In animal tissues, ChABC acts on chondroitin 4-sulfate, chondroitin 6-sulfate and dermatan sulfate. Chondroitin sulfate is the most abundant of the glycosaminoglycans in biological systems and includes a variety of sulfated and non-sulfated carbohydrate derivatives including sulfated glucuronic acid, N-acetylgalactosamine, and iduronic acid. These materials are often linked to proteins to form chondroitin sulfate proteoglycans (CSPG), which play a number of structural and functional roles in biological systems (e.g., cell-cell interactions with extracellular matrix, directing or inhibiting neurodevelopment, compositing cartilage to become a structural component). The biosynthesis of these CSPG molecules and the proper location are critical to the normal functioning of humans. In fact, many diseases associated with the lack of CSPG, accumulation, or dislocation, such as diffuse Lewy body disease, mucopolysaccharide disease IV-A type and mucopolysaccharide disease VII type, disc herniation and so on.

Chondroitinase enzymes are a group of enzymes that can be divided into four types with different activity and substrate specificity (chondroitinase ABC, chondroitinase AC, chondroitinase B and chondroitinase C). These enzymes, particularly chondroitinase ABC, have recently been shown to be potential new biological agents for the treatment of many CSPG-related diseases. For example, researchers have found that ChABC can significantly promote functional recovery of a damaged spinal cord. Other researchers have shown that the injection of chondroitin sulfate into the affected parts of keloid and/or hypertrophic scars can greatly improve the symptoms. There has also been developed a successful model for the treatment of rabbit disc herniation with ChABC. Recent scientific studies have suggested that ChABC has more potential medical applications, including the treatment of amblyopia, nerve and spinal cord injuries, posterior vitreous detachment and inhibition of tumor metastasis.

Whether ChABC can be successfully used as a biotherapeutic agent is significantly dependent on the production and purification of ChABC. ChABC's existing upstream production techniques are based on the fermentation of unmodified proteus vulgaris or recombinant expression hosts (e.g., E. coli). By appropriate optimization, both of these production methods can yield a large number of non-purified matrices containing ChABC enzyme with a host organism. Because the matrices contain substantial quantities of protein, nucleic acid, endotoxin, and other impurities, the development of efficient downstream purification methods for obtaining high purity ChABC is critical. Further, the amount and nature of impurities from different expression hosts are very different, so in order to purify ChABC from a particular expression host, a specific downstream purification procedure will typically be developed separately, especially when using only non-specific interaction ion exchange (IEX) or hydrophobic interaction (HIC) chromatography. However, the development and optimization of IEX/HIC chromatography is time-consuming and requires considerable manpower and material resources. Consequently, the typical process requires multiple IEX/HIC chromatography steps to achieve high purity target proteins resulting in high overall cost.

In contrast to IEX/HIC chromatography, affinity chromatography presents several potential advantages. In affinity chromatography, molecules or molecules that interact specifically with the target protein are partially immobilized on the chromatography filler. This highly selective interaction can effectively extract the desired protein and remove impurities. However, affinity chromatography has not been used as a purification tool for ChABC without affinity tag. Because ChABC is an enzyme, it is not easy to design affinity chromatography for native ChABC. This is because most of the known molecules that can specifically bind to native ChABC are ChABC substrates that will be degraded when combined with the ChABC enzyme. In other words, if these substrate molecules are immobilized on the stationary phase, they will be decomposed by the enzyme during the purification process, so that ChABC cannot be captured from the solution.

Thus there is a need in the art for novel purification techniques for ChABC to enable cost-effective production of ChABC for use as a biotherapeutic drug.

SUMMARY OF THE INVENTION

In order to solve the problems in the prior art, the inventors have found that heparin not only specifically binds to ChABC, but is not degraded at the time of binding. Based on this finding, the present invention provides a method for purifying ChABC from a matrix containing ChABC by chromatography using an affinity column immobilized with heparin.

In one embodiment, the present invention provides a specific affinity chromatography process for preparing high purity chondroitinase ABC from a matrix including chondroitinase ABC and a microorganism to produce chondroitinase ABC. The process comprises providing a matrix of material comprising one or more microorganisms to produce chondroitinase ABC, the microorganism selected from genetically-modified *Escherichia coli*, genetically-modified *Bacillus subtilis, Proteus vulgaris, Pichia pastoris*, and/or *Saccharomyces cerevisiae* and chondroitinase ABC produced by the microorganism. Cell debris are removed by centrifugation and adjusting the pH and conductivity of the matrix material.

A specific affinity heparin-immobilized chromatography column is provided comprising heparin immobilized on a resin, wherein the heparin-immobilized chromatography column is pre-equilibrated to a pH of approximately pH 7.0-7.5. The heparin-immobilized chromatography column is loaded with the pH- and conductivity-adjusted matrix material. The heparin-immobilized chromatography column loaded with matrix material is washed with washing liquid in two or more washes at a first pH and a second pH wherein the first pH is higher than the second pH to wash unwanted protein, DNA, and endotoxin and wherein at least one of the first and second pH is higher than the isoelectric point of chondroitinase ABC.

Chondroitinase ABC is eluted in a linear gradient solution of pH 6-9 NaCl to yield chondroitinase ABC at a purity of at least 98% and a yield of at least 70% in a single pass of the heparin-immobilized chromatography column.

In a further aspect, the washing liquid may be a pH 8-10 buffer.

In a further embodiment, endotoxin in the eluate of chondroitinase ABC may be removed by filtration after elution, optionally to less than 0.0002 EU/U.

In one aspect, the washing liquid may be a carbonate buffer, a phosphate buffer, a borate buffer, a Tris-HCl buffer or a Tris acetate buffer.

In an embodiment, the pH of the matrix containing chondroitinase ABC ABC is adjusted to 7.0.

In one aspect, the conductivity of the matrix including chondroitinase ABC is adjusted to 1-5 mS/cm.

In a further aspect, the heparin is immobilized on a resin for protein purification having a hydroxyl group, an amino group and/or a carboxyl group.

The resin may comprise one or more of agarose, cellulose, dextran, silica polyacrylamide or acrylic acid polymer.

In one aspect, the heparin is covalently bonded to the resin.

DETAILED DESCRIPTION OF THE INVENTION

Figure 1:
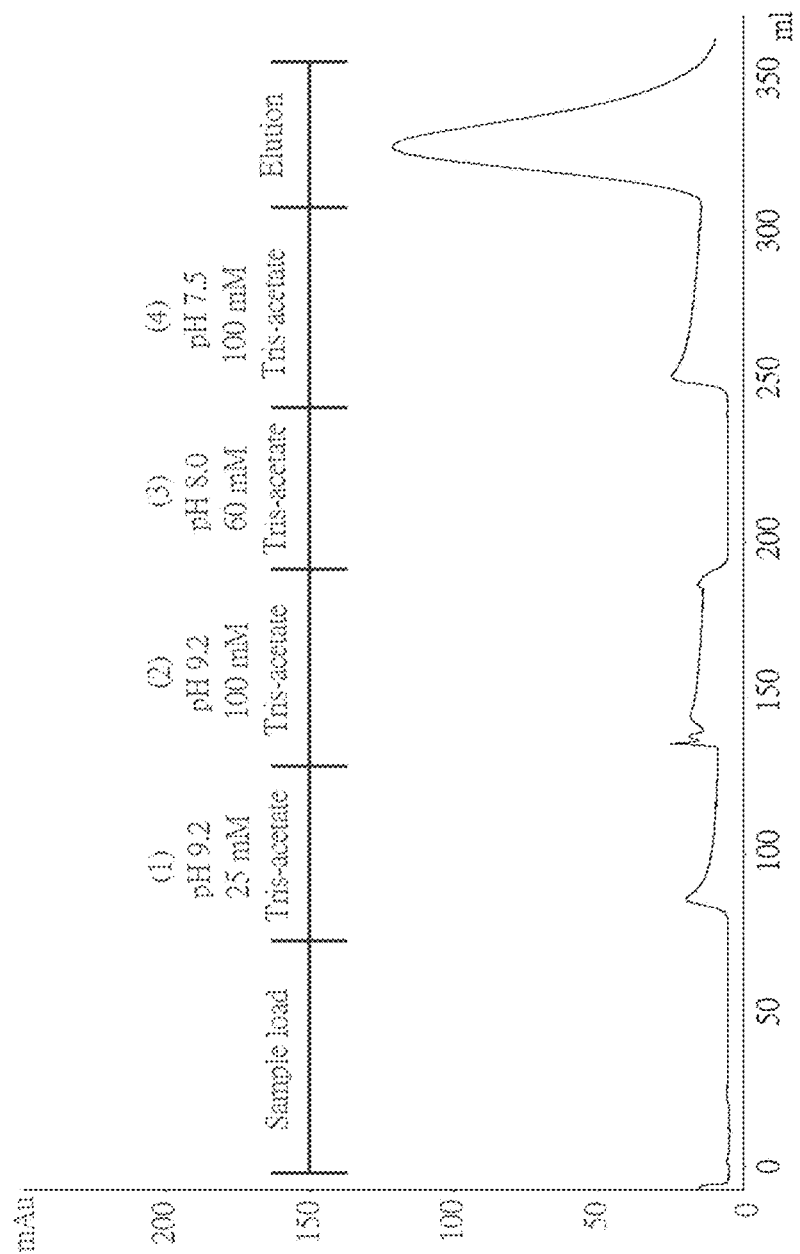
FIG. 1 shows a chromatogram of Example 2 of the present invention.

The present invention provides a novel and simple method for the purification of ChABC which can be applied to various ChABC-containing matrices. As used herein, the term "matrix" refers to a mixture of extracellular material or intracellular material (protein, DNA, lipid, etc.) from a host cell as a result of the host cell producing ChABC, along with the ChABC itself. The matrix may include bacteria, fungi, extracts containing surfactants, supernatants collected during fermentation, and other materials from the production of ChABC from a host material. The purification method is a chromatography method using an affinity column capable of selectively capturing ChABC. The affinity column is a column that binds to a specific ligand that specifically interacts with ChABC under chromatography conditions.

In an embodiment of the present invention, the ChABC, which is represented by the primary amino acid sequence of SEQ ID NO: 1, is either obtained from *Proteus vulgaris* or from the cell of the host material including but not limited to *Escherichia. coli, Bacillus subtillis, Proteus vulgaris, Pichia postoris, Saccharomyces cerevisiae*, etc. which recombinantly expresses the protein. The ChABC expressed from the recombinant host cell without additional processing contains an additional methionine (the amino acid sequence thereof is represented by SEQ ID NO: 2) at the N-terminal which is originated from the start codon "ATG". The N-terminal methionine can be removed to generate the mature ChABC with the amino acid sequence of SEQ ID NO: 1.

In the preparation of prokaryotic recombinant expression systems, the target gene for the expressed protein shall be cloned into an expression vector or integrated into the host's chromosomal DNA. In order to express the gene, start codon shall be present in the 5' end of the gene, which is translated into methionine at the N-terminal of the expressed protein. In many cases, the mature protein expressed in their natural host are naturally processed by other enzymes, for example, signal peptidase, during the extracellular exportation. In other words, the N-terminal of many naturally processed proteins contain no N-terminal methionine. Without introducing proper processing machinery, the recombinant protein will contain an additional and unnatural methionine at the N-terminal.

In order to produce a native protein without an additional N-terminal methionine, methionine aminopeptidase is usually cloned into the expression host and co-expressed with the recombinant target protein. Methionine aminopeptidase can remove the N-terminal methionine, but this enzyme has limited activity against the protein with charged or bulky amino acid residue at the P1' position. In addition, the activity of methionine aminopeptidase is dependent on the P2' position of the recombinant protein. Another strategy of generating recombinant protein with native sequence without additional N-terminal methionine is by utilizing protease that can digest the protein specifically and have no or low selectivity on the P1' position, i.e., without leaving a residue at the C-terminal side after the enzymatic digestion, after being purified from the host matrix. In this method, a DNA sequence encoding an affinity tag, e.g., maltose binding protein, His-tag, etc., are fused to the 5' end of the target gene. The protein expressed is therefore unnaturally tag-fused. However, the tag can be specifically removed by certain proteases, e.g., TEV protease, factor Xa, etc. Although this can effectively generate recombinant protein without additional methionine, the enzymatic digestion is conducted in vitro after the protein purification, and an additional chromatographic step is required to remove the protease.

To solve this problem, in the present invention, an engineered TEV protease that have a broad P1' selectivity is cloned into the expression host and co-expressed with ChABC gene of which a TEV protease recognition site (amino acid sequence ENLYFQ) has been added between the initial methionine and the native ChABC sequence.

For the recombinant bacterial expression system, the gene encoding the ChABC protein (SEQ ID NO: 3) is ligated into an expression vector containing promoter and Shine-Dalgarno (SD) sequence that can enable high transcription level in the host cell. Promoter of the vector used in *E. coli* expression system can be T7, T5, Lac, Trp, araC or any hybrid promoter of them. Promoter of the vector used in *B.*

*subtilis* can be Spac, SacB, Xyl, PBAD, Pgrac or any hybrid promoter of them. Apart from transforming the host bacteria with recombinant replicable expression vector, chromosomal integration of ChABC gene into the host bacteria can be another strategy for overexpression of ChABC. Some examples of chromosomal integration vector include pSG1112 (Liu et al., 2004) for the *B. subtilis* 1A304 (Φ105MU331) and pMG1 (Gimpel et al., 2012) for *B. subtilis* MG1P.

The expression of ChABC from *Proteus vulgaris* can be induced by introducing chondroitin sulfate, which is a known inducer for the production of the protein, into the culture medium through fed batch fermentation. In the recombinant expression system, the inducer is vector- and promoter-dependent, for example, IPTG for the lac promoter, arabinose for pBAD promoter. In the case of intracellularly expressed ChABC, the bacteria can be harvested by centrifugation or cross-flow microfiltration, depending on the scale of the fermentation. The extraction of ChABC from harvested bacteria can be either by mechanical disruption, for example, sonication, liquid homogenization, freeze-thaw, etc., or by chemical disruption, for example, introducing surfactant, lysozyme or any other lytic enzyme. ChABC in the extract or lysate is purified by the affinity chromatography method of the present invention.

To determine a suitable affinity material the inventors selected a large number of different types of polysaccharide derivatives such as glycosaminoglycans or other polysaccharides such as alginates, fucoidan, polygalacturonic acid, pentosan polysulfates, cellulose phosphates, etc. for determination of suitability for use in affinity chromatography. Although immobilization of the selected polysaccharide on the resin is the most direct way of testing the suitability of these ligands for ChABC affinity chromatography, the immobilization, ligand density, spacer groups, etc. between the ligand and the resin surface can significantly affect the interaction between ChABC and the immobilized polysaccharides. In other words, the determination of the binding between ChABC and polysaccharide in the solution phase is more appropriate and accurate for revealing the intensity of the interaction.

There are several existing methods for quantitative study of protein-small molecule interactions such as differential scanning calorimetry, quartz crystal microbalance, fluorescence anisotropy, and the like. However, these methods require complex equipment, are expensive and time consuming, requiring protein immobilization or protein labeling. In order to save time and reduce costs, semi-quantitative assessment methods can be applied, such as enzyme inhibition assays. In the present invention, the relative binding affinity is evaluated by monitoring the inhibition of ChABC by the selected polysaccharide. The stronger the observed inhibitory effect, the higher the affinity between the ChABC and the polysaccharide. A more detailed experimental setup is shown in Example 1. It was found that heparin almost completely inhibited ChABC activity when an equal amount of substrate (chondroitin sulfate C) was administered by enzyme inhibition assay. Thus, heparin was identified as the most suitable ligand among the selected screened polysaccharides for constructing the affinity column.

In the present invention, heparin may be immobilized on different resins having a hydroxyl, amino, and carboxyl group for ligand immobilization. Heparin may be covalently bonded to the resin. For the resin, the present invention is not particularly limited as long as heparin can be covalently bonded to the resin. Selected resins include, but are not limited to agarose, cellulose, dextran, silica polyacrylamide, or acrylic polymers. The heparin or resin may be activated by various activators including, but not limited to, cyanogen bromide, EDC/NHS (1-ethyl-3-(3-dimethylaminopropyl) carbodiimide/succinimide), sodium periodate, epichlorohydrin, and the like.

In the present invention, the affinity column to which heparin is immobilized, particularly covalently bound to heparin, does not require further coating. In particular, the column is not further coated with glycosaminoglycans which are degraded by ChABC. Optionally, further coating is feasible without the use of glycosaminoglycans.

Although heparin can bind and can significantly inhibit ChABC, the affinity between immobilized heparin and ChABC in chromatography is unknown. To demonstrate that ChABC still has affinity for immobilized heparin, the purified ChABC was loaded into a chromatography column of heparin coupled via amide bonds to crosslinked agarose beads and washed with the various buffers described in Example 2. In fact, Tris acetate buffer (pH 9.2) that has a pH above the isoelectric point (pI=8.5) of ChABC was applied to the column. At the pI, ChABC becomes negative, and negatively-charged ChABC and the negatively-charged heparin on the resin should repel each other. If ChABC has only a non-specific charge interaction with heparin, it will elute from the column. However, from the experimental results, ChABC was not only successfully captured by the resin, but was not eluted by a buffer having a pH above the pI. In other words, ChABC has a specific interaction with heparin, rather than pure nonspecific charge interactions.

In the present invention, the ChABC affinity chromatography column using heparin has a significant advantage over the most commonly used cation exchange column for ChABC purification because of the significantly lower amount of impurities that are non-specifically bound to the resin. Thus, the affinity chromatography of the present invention can be applied to various matrices with different impurity spectra including, but not limited to, *Escherichia coli, Bacillus subtilis, Proteus vulgaris*, Yeast (*Pichia pastoris* and/or *Saccharomyces cerevisiae*), to obtain highly purified ChABC. However, since heparin is a negatively charged polysaccharide, a small amount of positively charged protein may still be non-specifically captured by heparin immobilized resin. However, it was determined that these nonspecific binding proteins can be removed by application of high pH buffers (pH 8-10). Selected pH 8-10 buffers include carbonate buffer, phosphate buffer, borate buffer, Tris —HCl buffer or Tris acetate buffer, such as sodium carbonate buffer, sodium phosphate buffer, potassium carbonate buffer, potassium phosphate buffer, sodium borate buffer, potassium borate buffer. Buffers in this pH range can significantly reduce nonspecific protein interactions because most of the protein impurities will become negatively charged and therefore do not interact with the heparin immobilized resin with charge. The effect of ChABC is not affected by the high pH buffers. After removal of protein impurities, ChABC was eluted with a linear gradient of NaCl at pH 6-9. The eluate may contain ChABC (Examples 3-5) having a purity of up to 98-99% or more and having a low endotoxin level. The endotoxin can be further removed by passing the eluate through an endotoxin capture filter. In addition to low endotoxin and protein impurities, another advantage of this process is simplicity and high recovery. Single-step chromatography significantly reduces the processing time, thus avoiding the loss of activity during processing. In fact, the final yield is in the range of 70-80% (Examples 3-5), which is significantly higher than all existing methods. More importantly, affinity chromatography can be applied to different types of substrates produced by different host cells.

Example 1

In the present invention, it is necessary to identify molecules that have a similar structure to the substrate of ChABC but are inert to enzymatic degradation. In order to test polysaccharides that could actually bind to the active site of ChABC, a relative enzyme inhibition assay was conducted on the selected polysaccharide:

490 μL of the substrate solution was incubated at 37° C. for at least 15 minutes containing 0.2% chondroitin sulfate C, 0.2% selected polysaccharide and 50 mM pH8 Tris HCl buffer. 10 μL of ChABC with activity of about 100 U/L was incubated at 37° C. for at least 3 minutes. After incubation, the two solutions were gently mixed. The mixture was then incubated at 37° C. for 20 minutes to perform enzymatic degradation of chondroitin sulfate. After 20 minutes, the reaction was terminated by inactivating ChABC by heating at 100° C. for 2 minutes. In addition to inactivating the mixture immediately without incubation for 20 minutes, a blank control was performed in the same manner. The absorbance of the heat inactivated solution at 232 nm was then measured and the apparent activity was calculated as shown in Equation 1. The assay in the absence of selected polysaccharide was also conducted in the same manner as a reference. The calculation of the percentage of inhibition was showed in Equation 2:

$$U/L = \frac{Abs}{E \times t} \times \frac{Vt}{Vs} \times 1000 \times DF \quad \text{(Equation 1)}$$

where

Abs=Difference in absorbance

=$OD_{232nm}$ in sample tubes−$OD_{232nm}$ in blank tubes

E=Millimolar extinction coefficient of unsaturated disaccharides from Chondroitin Sulfate C=5.5 t=Reaction time=20 min

Vt=Total volume of the assay=0.5 mL

Vs=Volume of enzyme used=0.01 mL

DF=Dilution factor

1000=Convert U/mL to U/L $$\%in = \frac{A(poly)}{A(ref)} \times 100\% \quad \text{(Equation 2)}$$

where

% rA=percentage of residual activity

A(poly)=the activity presence of selected polysaccharide

A(ref)=the absorbance of the assay without the presence of selected polysaccharide Among all polysaccharides, alginate and polygalacturonic acid had no significant effect on enzyme activity, whereas heparin had the strongest inhibitory effect on ChABC. The results of the relative enzyme inhibition assays are shown in Table 1:

TABLE 1

| Sample | Reference | Heparin | Polygalacturonic acid | Alginic acid |
|---|---|---|---|---|
| Activity (U/L) | 121 | 5.1 | 117 | 119 |
| % rA | NA | 4.2 | 97 | 98 |

Furthermore, as incubation of ChABC alone with the heparin does not give any change in absorbance, heparin is not subject to the enzymatic degradation activity of ChABC. Therefore, immobilization of heparin as a ligand for affinity purification of ChABC is the most suitable choice among the selected polysaccharide derivatives.

Example 2

To test whether ChABC has a specific interaction with immobilized heparin, a column filled with heparin coupled via amide bonds to crosslinked agarose beads was used. The column was pre-equilibrated with 25 mM Tris-acetate (pH 7.3) before loading the sample onto the column. ChABC was dissolved in 25 mM Tris-acetate (pH 7.5) and loaded onto a column. (1) 25 mM Tris-acetate (pH 9.2), (2) 100 mM Tris-acetate (pH 9.2), (3) 60 mM Tris-acetate (pH 8) and (4) 100 mM Tris-Acetate (pH 7.5). None of these buffers elute ChABC from the column. And when the 0-0.3M NaCl linear gradient is applied, ChABC can be eluted from the column. The chromatogram is shown in FIG. 1.

Example 3

Gene encoding ChABC (SEQ ID NO: 1) from *P. vulgaris* was cloned by conventional PCR from the genomic DNA of *P. vulgaris*. This PCR product contain the DNA sequence encoding ChABC (SEQ ID NO:1) was used as a template for the second round PCR during which it was decided to add the DNA sequence encoding MGSENLYFQ to the N-terminal of the ChABC, so that the DNA sequence encoding TEV protease-recognition-site contained ChABC (SEQ ID NO: 3) was generated. The PCR product was ligated via T4 DNA ligase to linearized pET3a to form a recombinant plasmid with the encoding sequence of native ChABC. The recombinant plasmid was then introduced into *E. coli* strain BLR (DE3) by electroporation. The transformed *E. coli* was plated on LB agar plate containing 50 μg/ml ampicillin to allow selection of colonies transformed with the plasmid. The selected single colony was inoculated into LB medium at 37° C. with 50 μg/ml ampicillin for 18 hours as a pre-culture and this pre-culture was transferred into another LB culture medium at 37° C. containing 50 μg/ml ampicillin in the ratio 1:100. This other culture medium was further incubated at 37° C. until the OD600 reached 0.8. IPTG at 1 mM was added to the culture medium for inducing the production of ChABC to progress further 4 hours. The cell mass was harvested by centrifugation and stored at −80° C.

10 g of recombinant *E. coli* cells were resuspended in 25 mM Tris HCl (pH 7.0) and subjected to sonication for 5 minutes. Cell debris were removed from the suspension by centrifugation at 17000 g for 1 hour. The supernatant was collected and the pH was adjusted to pH 7.0 by the addition of NaOH. The conductivity of the supernatant was adjusted to 1.2 mS/cm by the addition of double deionized water.

Figure 2:
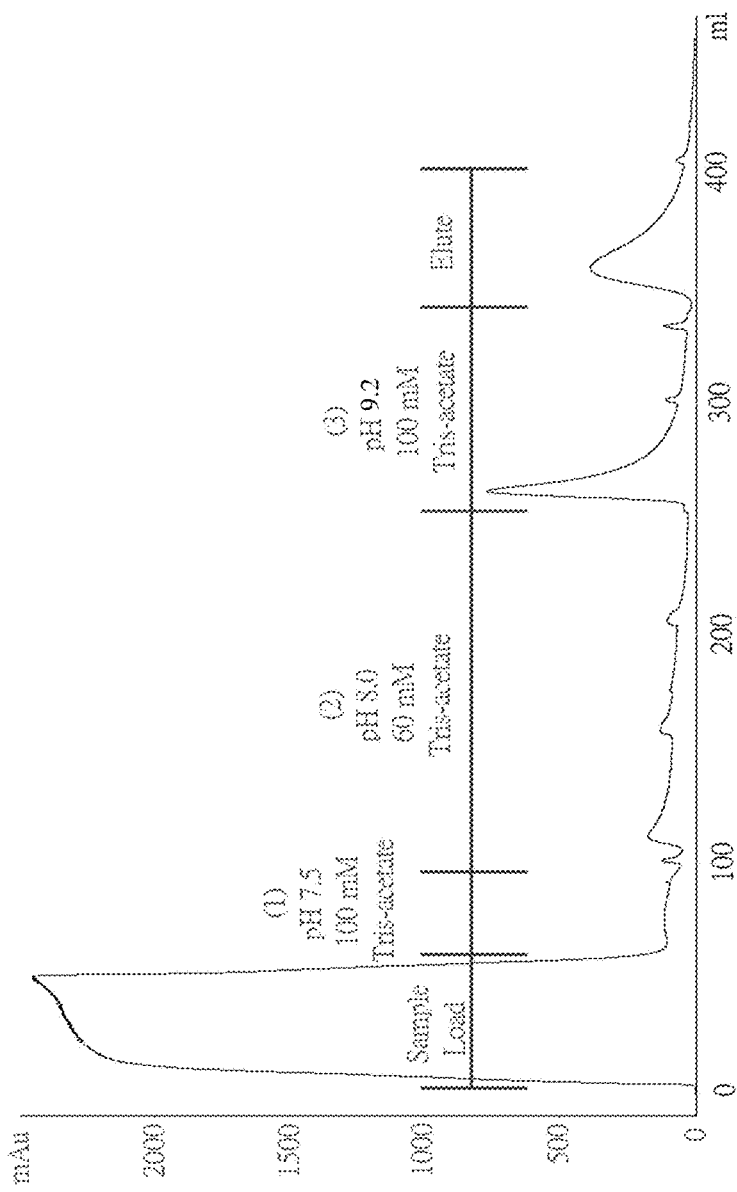
FIG. 2 shows a chromatogram of Example 3 of the present invention.
Figure 3:
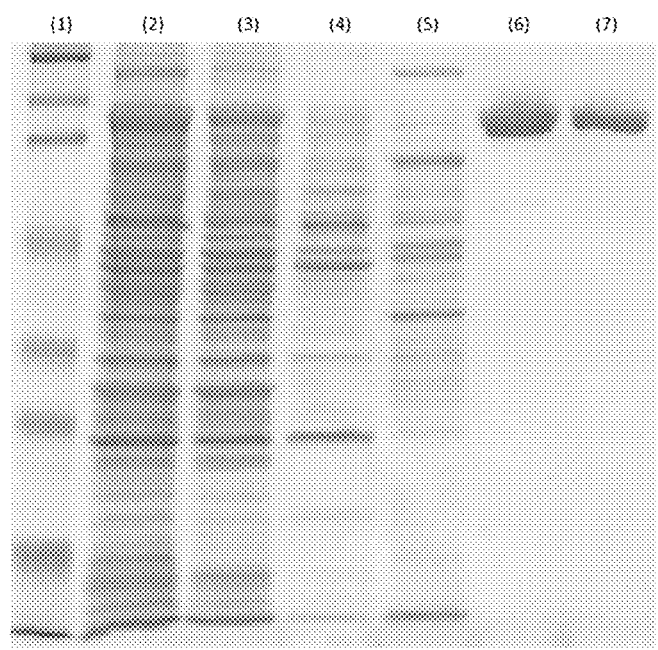
FIG. 3 shows an SDS-PAGE diagram of Example 3 of the present invention.

The supernatant containing ChABC was subjected to 0.22 μm filtration prior to loading onto a heparin immobilized column with pH 7.5 25 mM Tris-acetate pre-equilibrated. The column was then washed with (1) 100 mM Tris-acetate (pH 7.5), (2) 60 mM Tris-acetate (pH 8), (3) 100 mM Tris-acetate (pH 9.2) Of ChABC was linearly eluted by 0-0.5 M NaCl. The chromatogram and SDS-PAGE are shown in FIG. 2 and FIG. 3.

The degree of purification in the above method is shown in Table 2.

TABLE 2

|  | Total activity (U) | Recovery yield (%) |
|---|---|---|
| Supernatant before chromatography | 3034 | — |
| Flow through | 5 | — |
| Wash 1 | <1 | — |
| Wash 2 | <1 | — |
| Wash 3 | <1 | — |
| Eluate | 2998 | 76 |

It can be seen that the method of this example is capable of obtaining ChABC with a purity of >99%, a recovery rate of 76% and an endotoxin level below 0.0002 EU/U.

Example 4

Gene encoding ChABC (SEQ ID NO: 1) from *P. vulgaris* was cloned by conventional PCR from the genomic DNA of *P. vulgaris*. This PCR product contain the DNA sequence encoding ChABC (SEQ ID NO:1) was used as a template for the second round PCR which was decided to add the DNA sequence encoding MGSENLYFQ to the N-terminal of the ChABC, so that the DNA sequence encoding TEV protease-recognition-site contained ChABC (SEQ ID NO: 3) was generated. The PCR product was ligated via T4 DNA ligase to linearized pHT43 to form a recombinant plasmid with the encoding sequence of native ChABC. The recombinant plasmid was then introduced into *B. subtilis* 168 by electroporation. The transformed *B. subtilis* was plated on a 2×TY agar plate containing 5 μg/ml chloramphenicol to allow selection of colonies transformed with the plasmid. The selected single colony was inoculated into a sterile 2×TY medium at 37° C. with 5 μg/ml chloramphenicol for 18 hours as a pre-culture and this pre-culture was transferred into another sterile 2×TY culture medium at 37° C. containing 5 μg/ml chloramphenicol in the ratio 1:100. This another culture medium was further incubated at 37° C. until the OD600 reached 0.8. IPTG at 1 mM was added to the culture medium for inducing the production of ChABC to progress further 4 hours. The cell mass was harvested by centrifugation and stored at −80° C.

5 g of recombinant *B. subtilis* cells were resuspended in 25 mM Tris-acetate (pH 7.0) incubated with 1 μg/ml lysozyme for 20 min at 30° C. The bacterial cells were further lysed by sonication for 5 minutes. Cell debris was removed from the suspension by centrifugation at 17000 g for 1 hour. The supernatant was collected and the pH was adjusted to pH 7.0 by introduction of NaOH. The conductivity of the supernatant was adjusted to 1.6 mS/cm by the introduction of double deionized water.

Figure 4:
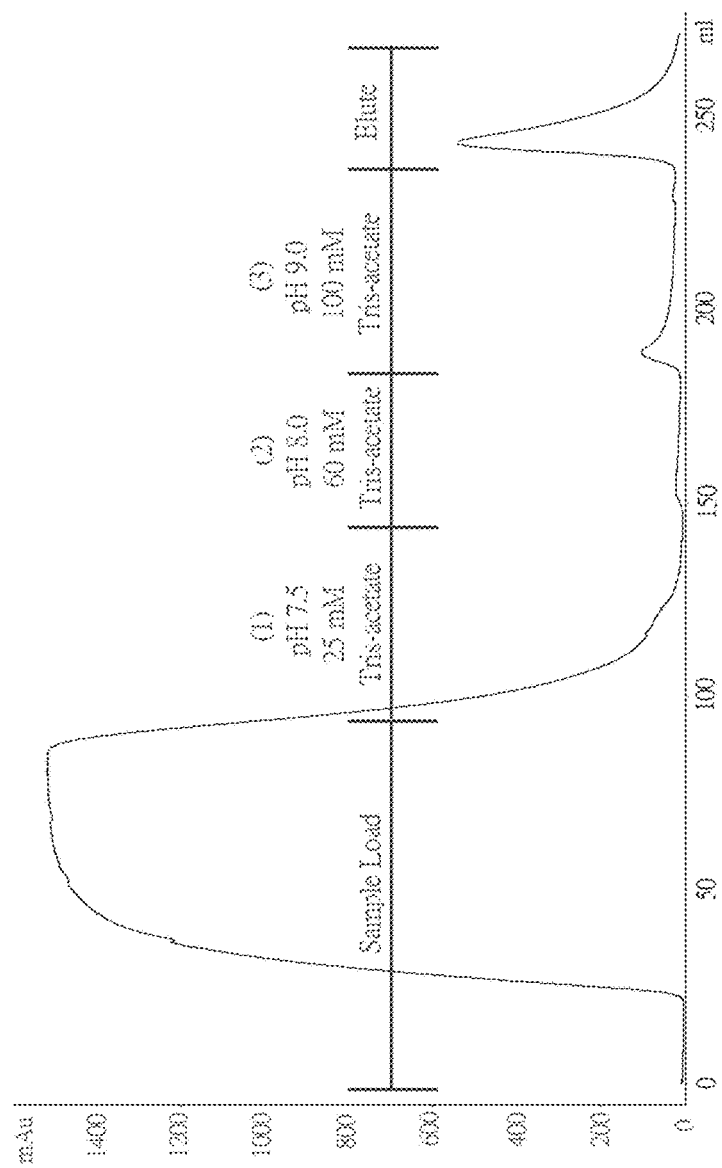
FIG. 4 shows a chromatogram of Example 4 of the present invention.
Figure 5:
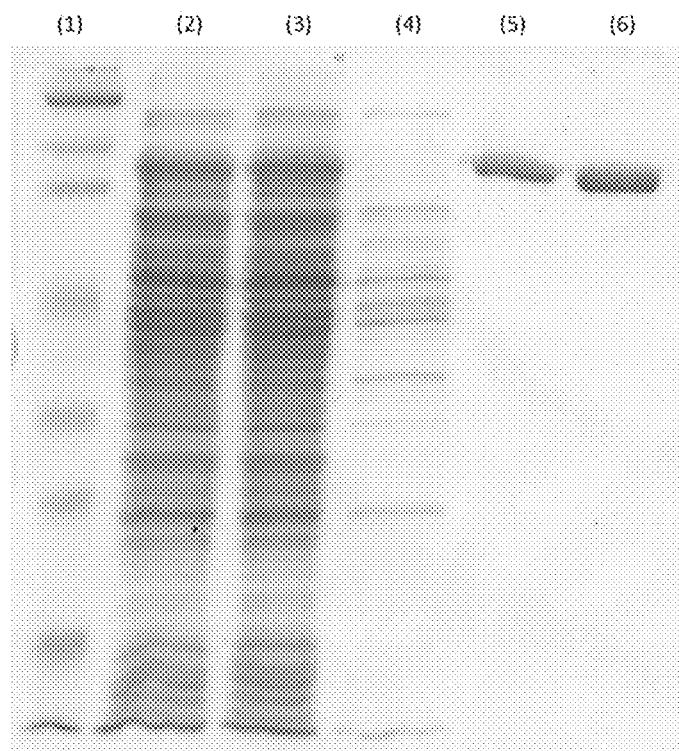
FIG. 5 shows an SDS-PAGE diagram of Example 4 of the present invention.

The supernatant containing ChABC was subjected to 0.22 μm filtration prior to loading onto a heparin immobilized column with pH 7.5 25 mM Tris-acetate pre-equilibrated. The column was then washed with (1) pH 7.5 25 mM Tris-acetate, (2) pH 8 60 mM Tris acetate, (3) pH 9 100 mM Tris acetate. The ChABC on the column was eluted with a linear gradient of 0-0.5 M NaCl. The chromatogram is shown in FIG. 4 and FIG. 5. The degree of purification is shown in Table 3.

TABLE 3

|  | Total activity (U) | Recovery yield (%) |
|---|---|---|
| Supernatant before chromatography | 2610 | — |
| Flow through | <1 | — |
| Wash 1 | <1 | — |
| Wash 2 | <1 | — |
| Wash 3 | <1 | — |
| Eluate | 1931 | 74 |

It can be seen that the method of this example is capable of obtaining ChABC with a purity of >99%, a recovery rate of 74% and an endotoxin level below 0.0002 EU/U.

Example 5

Figure 6:
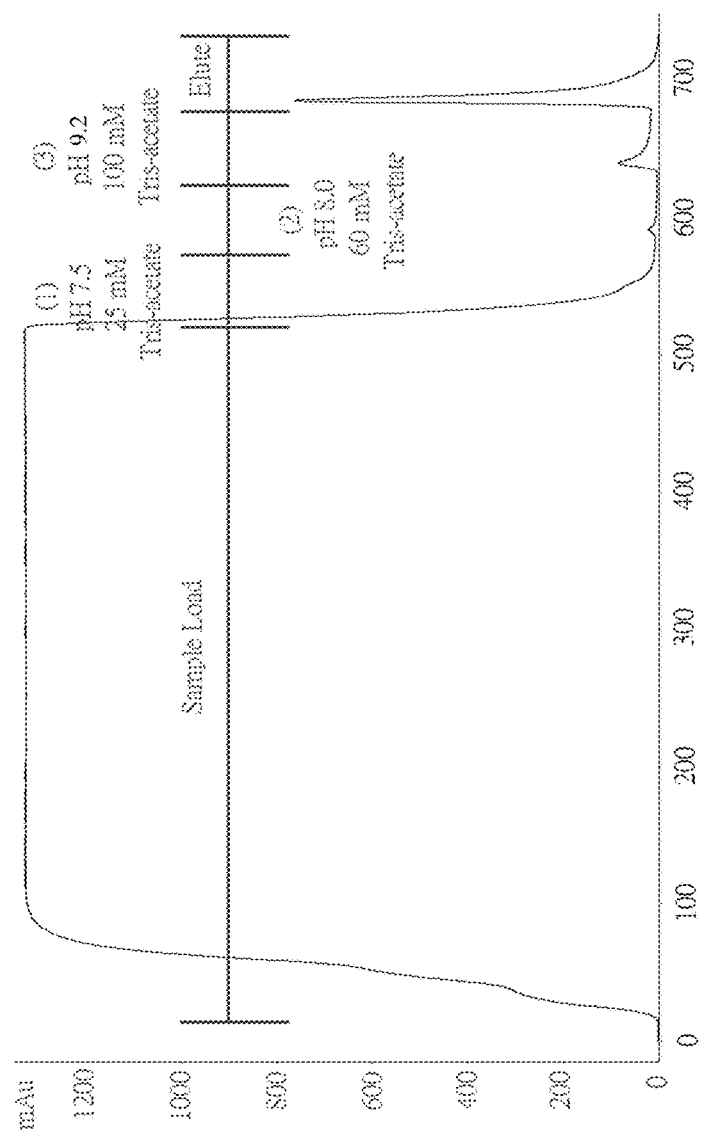
FIG. 6 shows a chromatogram of Example 5 of the present invention.
Figure 7:
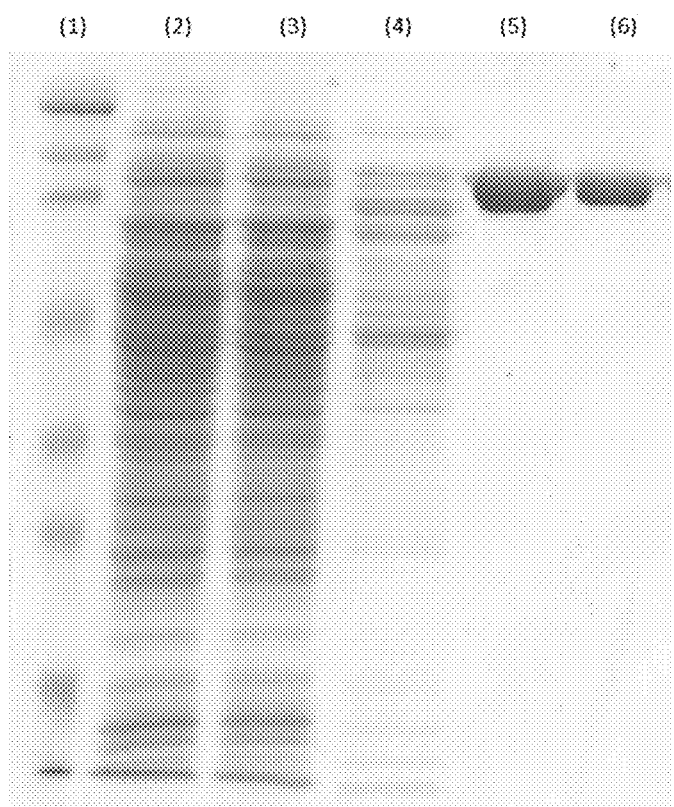
FIG. 7 shows an SDS-PAGE diagram of Example 5 of the present invention.

The cell paste of 25 g of *Proteus vulgaris* was resuspended in 25 mM Tris-acetate (pH 7.0) containing 2% Triton X-100 preheated at 37° C. for 30 minutes. The suspension was stirred continuously at 750 rpm and incubated at 37° C. for 2 hours. After extraction, the suspension was diluted 2-fold with 4-6° C. high-purity water. The diluted suspension was then immediately clarified by high-speed centrifugation at 17700 g centrifugation. The supernatant was further clarified by filtration through a micropore with a pore size of 0.2 μm. The pH of the clarified supernatant was adjusted to pH 7.0, the conductivity was adjusted to 4.8 mS/cm, and then loaded onto the heparin immobilized column. The heparin immobilized column was pre-equilibrated with pH 7.0 25 mM Tris-acetate. After the supernatant was completely loaded onto the column, the column was washed with (1) pH 7.0 25 mM Tris-acetate, (2) pH 8.0 60 mM Tris-acetate and (3) pH 10 100 mM Tris-Acetate 9.2 to remove impurities that include unwanted proteins, DNA, endotoxin. ChABC was eluted with a linear gradient of 0-0.5 M NaCl and tested for endotoxin levels below 0.0002 EU/U. Purified chromatograms are shown in FIG. 6 and FIG. 7. The degree of purification is shown in Table 4.

TABLE 4

|  | Total activity (U) | Recovery yield (%) |
|---|---|---|
| Supernatant before chromatography | 2810 | — |
| Flow through | <1 | — |
| Wash 1 | <1 | — |
| Wash 2 | <1 | — |
| Wash 3 | <1 | — |
| Eluate | 2248 | 81 |

It can be seen that the method of this example is capable of obtaining ChABC with a purity of >99%, a recovery rate of 81% and endotoxin levels below 0.0002 EU/U.

Those skilled in the art, with the guidance of the above teachings, may make various modifications and variations with respect to the invention. It is therefore to be understood that the invention may be practiced otherwise than as specifically described herein without departing from the spirit of the invention as set forth in the claims.

The invention claimed is:

1. A matrix of a material comprising one or more microorganism(s) to produce chondroitinase ABC, the microorganisms selected from genetically-modified *Escherichia coli*, genetically-modified *Bacillus subtilis, Proteus vulgaris, Pichia pastoris*, and/or *Saccharomyces cerevisiae*; and wherein said one or more microorganism(s) expresses or expressed the chondroitinase ABC comprising the amino acid sequence set forth in SEQ ID NO: 3.

2. The matrix of a material of claim 1, wherein said matrix is a mixture of extracellular or intracellular material from said one or more microorganisms.

3. The matrix of a material of claim 1, further comprising extracts containing surfactants, supernatants collected during fermentation, and/or other materials from the production of chondroitinase ABC by said microorganisms.

4. The matrix of a material of claim 1, wherein said microorganisms are transformed by an expression vector containing an encoding sequence of said chondroitinase ABC, a promoter, and Shine-Dalgarno sequence that enables high transcription level in the transformed microorganisms.

5. The matrix of a material of claim 4, wherein said promoter comprises T7, T5, Lac, Trp, araC, Spac, SacB, Xyl, PBAD, Pgrac, or any combination thereof.

6. The matrix of a material of claim 1, wherein said microorganisms are integrated with the genes of said chondroitinase ABC into corresponding chromosome(s) of said microorganism for over-expression of said chondroitinase ABC.

7. The matrix of a material of claim 6, wherein said genes are integrated into the chromosome(s) of said microorganism via a chromosomal integration vector comprising pSG1112 and pMG1.

8. The matrix of a material of claim 1, wherein said chondroitinase ABC is over-expressed by said microorganism in the presence of an inducer being introduced into a culture medium of said microorganisms through fed batch fermentation.

9. The matrix of a material of claim 8, wherein said inducer is chondroitin sulfate.

* * * * *